(12) United States Patent
Miller et al.

(10) Patent No.: US 11,786,234 B2
(45) Date of Patent: Oct. 17, 2023

(54) KNOTLESS SUTURE ANCHOR CONSTRUCT

(71) Applicant: Conmed Corporation, Utica, NY (US)

(72) Inventors: Peter Miller, Largo, FL (US); Adrian Bosworth, Bradenton, FL (US)

(73) Assignee: Conmed Corporation, Utica, NY (US)

( * ) Notice: Subject to any disclaimer, the term of this patent is extended or adjusted under 35 U.S.C. 154(b) by 438 days.

(21) Appl. No.: 16/975,579

(22) PCT Filed: Feb. 27, 2019

(86) PCT No.: PCT/US2019/019715
§ 371 (c)(1),
(2) Date: Aug. 25, 2020

(87) PCT Pub. No.: WO2019/168891
PCT Pub. Date: Sep. 6, 2019

(65) Prior Publication Data
US 2020/0405282 A1    Dec. 31, 2020

Related U.S. Application Data

(60) Provisional application No. 62/637,134, filed on Mar. 1, 2018, provisional application No. 62/637,106, filed
(Continued)

(51) Int. Cl.
*A61B 17/04* (2006.01)
(52) U.S. Cl.
CPC .. *A61B 17/0401* (2013.01); *A61B 2017/0406* (2013.01); *A61B 2017/0459* (2013.01); *A61B 2017/0464* (2013.01)
(58) Field of Classification Search
CPC ........ A61B 17/0401; A61B 2017/0406; A61B 2017/0459; A61B 2017/0409;
(Continued)

(56) References Cited

U.S. PATENT DOCUMENTS 8,652,172 B2    2/2014 Denham et al.
8,795,334 B2    8/2014 Astorino et al.
(Continued)

FOREIGN PATENT DOCUMENTS

WO    2014/134185    9/2014
WO    WO2016154099 A2    9/2016

OTHER PUBLICATIONS

KR Office Action, App. No. 10-2020-7027180, dated Sep. 21, 2022, pp. 3-9.
(Continued)

*Primary Examiner* — Katherine M Shi
(74) *Attorney, Agent, or Firm* — BOND, SCHOENECK & KING, PLLC; Frederick Price

(57) ABSTRACT

A knotless suture anchor construct for securing a tissue in a desired position relative to a bone hole. The construct includes a substrate having a first end and a second end, and a filament woven through a plurality of passing locations along the substrate. The filament forms a first loop extending to a passing limb and reducing limb. There is a passing portion in the reducing limb between two adjacent passing locations of the plurality of passing locations. In a pre-deployment configuration, the first loop of the filament extends from a first end of the substrate and the passing limb and the reducing limb extend from the second end of the substrate. Also, in the pre-deployment configuration, the passing portion extends through the first loop, forming a second loop in the reducing limb.

13 Claims, 21 Drawing Sheets

Related U.S. Application Data on Mar. 1, 2018, provisional application No. 62/636,906, filed on Mar. 1, 2018.

(58) Field of Classification Search
CPC ...... A61B 2017/0464; A61B 17/06166; A61B 2017/0404; A61B 2017/0414; A61B 17/07292; A61F 2/0811
See application file for complete search history.

(56) References Cited

U.S. PATENT DOCUMENTS

| | | | |
|---|---|---|---|
| 2014/0243859 A1* | 8/2014 | Robinson | A61B 17/00234 606/151 |
| 2016/0270777 A1* | 9/2016 | Miller | A61B 17/0401 |
| 2018/0049734 A1 | 2/2018 | Kam | |

OTHER PUBLICATIONS

International Search Report Form PCT/ISA/220, International Application No. PCT/US2019/019715, pp. 1-10, dated Jun. 7, 2019.

\* cited by examiner

KNOTLESS SUTURE ANCHOR CONSTRUCT

CROSS-REFERENCES TO RELATED APPLICATIONS

This application is a national stage application under 35 U.S.C. 371 based on international patent application PCT/US19/19715 filed on Feb. 27, 2019, which claims priority to U.S. Provisional Patent Application Ser. No. 62/636,906, filed on Mar. 1, 2018 and entitled "Knotless All-Suture Anchor," U.S. Provisional Patent Application Ser. No. 62/637,106, filed on Mar. 1, 2018 and entitled "Knotless All-Suture Anchor," and U.S. Provisional Patent Application Ser. No. 62/637,134, filed on Mar. 1, 2018 and entitled "Knotless All-Suture Anchor," the entireties of which are incorporated herein by reference.

BACKGROUND OF THE INVENTION

1. Field of the Invention

The present invention is directed generally to suture anchors and, more particularly, to a knotless suture anchor construct for securing a tissue in a desired position relative to a bone hole.

2. Description of Related Art

Surgical procedures often call for suture anchors to provide a reliable attachment location for sutures in and/or against a substrate. The attached sutures are then used to capture and retain other objects including soft tissue. The substrate may be bone or boney material or soft tissue. For bone and like boney material, suture anchors can be inserted into a pre-formed hole in the bone so that the attached suture extends from the suture anchor out of the pre-formed hole. Where the substrate is soft tissue, suture anchors can reside on a side of the soft tissue so that the suture extends from the suture anchor, through a hole in the tissue, and further beyond the soft tissue on a side opposite the soft anchor.

In conventional practice, suture anchors can incorporate at least one feature to generate a retention capacity to retain the suture anchor in the pre-formed hole. In some anchors, the feature embodies a ridged member that can deform to create an interference fit with the substrate. Other suture anchors utilize an external feature (e.g., a barb, screw threads(s), etc.). These external features can interact with the substrate to create the retention capacity, often by piercing, cutting, and/or deforming the substrate. In still other suture anchors, the feature may be moveable (e.g., a deployable barb) that translates to create the retention capacity.

Many factors can have a direct effect on the actual retention capacity achieved by any suture anchor. For example, the quality of tissue, bony or soft, may increase or decrease the retention capacity by a large degree depending on the design of a particular suture anchor. Thus, some suture anchors perform well in certain circumstances while other anchors perform better in other circumstances. Similarly, the quality of installation affects the retention capacity.

Therefore, there is a need for a suture material interleaved into a soft, malleable substrate to form a loop configuration to pull repair sutures into a pre-formed hole and to deform the substrate.

Description of the Related Art Section Disclaimer: To the extent that specific patents/publications/products are discussed above in this Description of the Related Art Section or elsewhere in this disclosure, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Description of the Related Art Section and/or throughout the application, the descriptions/disclosures of which are all hereby incorporated by reference into this document in their respective entirety(ies).

SUMMARY OF THE INVENTION

The present invention is directed to a knotless suture anchor construct that is optimal for securing a tissue in a desired position relative to a bone hole. According to one aspect, the knotless suture anchor construct includes a substrate having a first end and a second end, and a filament woven through a plurality of passing locations along the substrate. The filament forms a first loop extending to a passing limb and a reducing limb. There is passing portion in the reducing limb between two adjacent passing locations of the plurality of passing locations. In a pre-deployment configuration, the first loop of the filament extends from the first end of the substrate and the passing limb and the reducing limb extend from the second end of the substrate. Also, in the pre-deployment configuration, the passing portion extends through the first loop, forming a second loop in the reducing limb.

According to another aspect, the knotless suture anchor construct includes a filament having a splice between a passing limb and a reducing limb. The passing limb extends through the splice, creating a first loop. The construct also includes a substrate having a first end and a second end. In a pre-deployment configuration, the filament is woven through the substrate such that the passing limb extends through a first passing location on the first end of the substrate and the reducing limb extends through one or more passing locations toward the second end of the substrate. There is a passing portion in the reducing limb between two adjacent passing locations of the one or more passing locations toward the second end of the substrate. In the pre-deployment configuration, the passing portion extends through the first loop, forming a second loop in the reducing limb.

According to another aspect, the present invention is a method for securing an object in position relative to a bone hole. The method includes the steps of: (i) providing a knotless suture anchor construct comprising a substrate having a first end and a second end, a filament woven through a plurality of passing locations along the substrate, the filament forming a first loop extending to a passing limb and reducing limb, wherein the first loop of the filament extends from the first end of the substrate and the passing limb and the reducing limb extend from the second end of the substrate, and a passing portion in the reducing limb between two adjacent passing locations of the plurality of passing locations, wherein the passing portion extends through the first loop forming a second loop in the reducing limb; (ii) inserting the knotless suture anchor construct into a bone hole; (iii) passing the passing limb around the object and then through the second loop; and (iv) tensioning the reducing limb to decrease the size of the second loop.

These and other aspects of the invention will be apparent from and elucidated with reference to the embodiment(s) described hereinafter.

The discussion below describes embodiments of a suture anchor that is configured to pull repair sutures into a pre-formed hole in bone or boney tissue. These configurations can have a filament (e.g., a suture) interwoven into a soft, malleable substrate (e.g., suture ribbon). The interwoven filament can form loops to receive free-ends of the repair suture that originates from a fixation site adjacent the pre-formed hole. In use, tension on free-ends of the interwoven filament can translate the loops to engage the repair suture, effectively pulling the free-ends into the pre-formed hole and interleaving the repair suture with the substrate in a manner that allows the filament to freely translate through the substrate and relative to the repair suture.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following description taken in conjunction with the accompanying drawings in which:

DETAILED DESCRIPTION OF THE INVENTION

Aspects of the present invention and certain features, advantages, and details thereof, are explained more fully below with reference to the non-limiting examples illustrated in the accompanying drawings. Descriptions of well-known structures are omitted so as not to unnecessarily obscure the invention in detail. It should be understood, however, that the detailed description and the specific non-limiting examples, while indicating aspects of the invention, are given by way of illustration only, and are not by way of limitation. Various substitutions, modifications, additions, and/or arrangements, within the spirit and/or scope of the underlying inventive concepts will be apparent to those skilled in the art from this disclosure.

Figure 1:
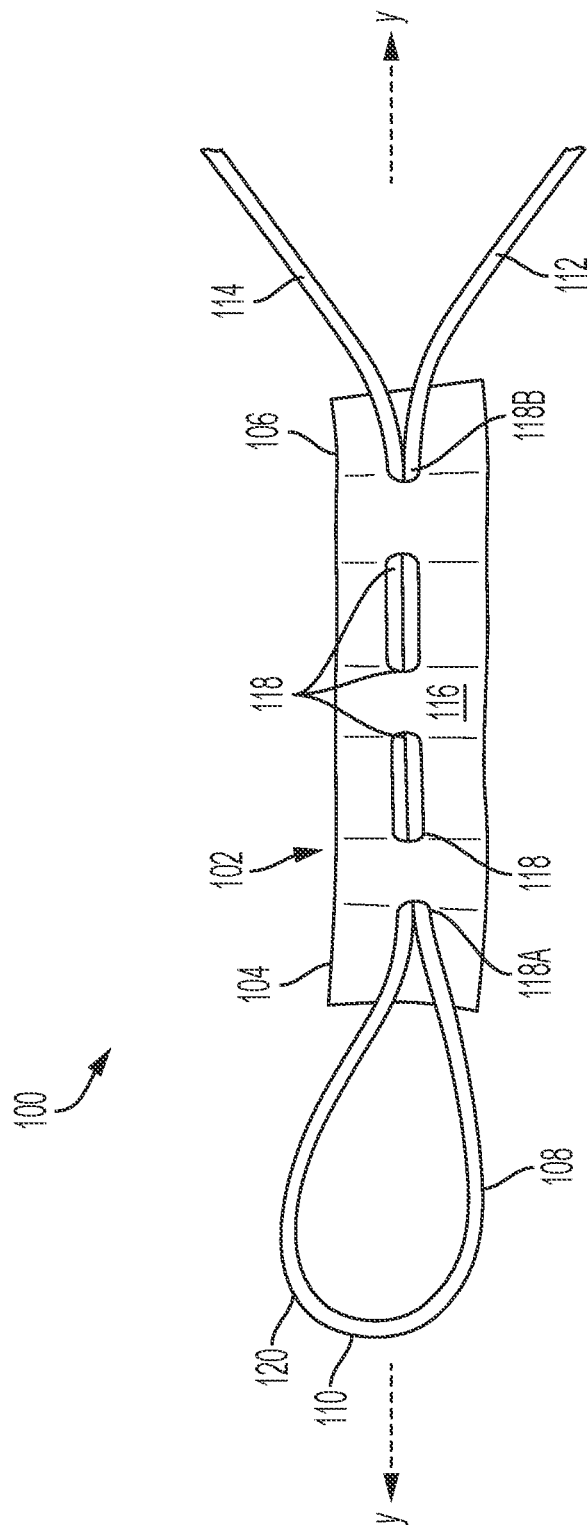
FIG. 1 is a top view schematic representation of a knotless suture anchor construct in a planar configuration, according to an embodiment.

Referring now to the figures, wherein like reference numerals refer to like parts throughout, FIG. 1 shows a top view schematic representation of a knotless suture anchor construct 100 in a planar configuration, according to an embodiment. The knotless suture anchor construct 100 comprises a substrate 102 having and extending between a first end 104 and a second end 106 along a central longitudinal y-y axis. The substrate 102 can be any suture material, such as the Y-Knot® suture tape. In the depicted embodiment, the substrate 102 is rectangular, although other shapes and configurations can be used.

The knotless suture anchor 100 additionally comprises a first filament 108 woven through substrate 102. The filament 108 can be composed of any suture material. In the preferred embodiment, the filament 108 is composed of hollow suture braid, which flattens and does not flip as much as round suture (but can be round, flat, and/or include or not include a core). In the first configuration, the filament 108 is folded at a central section 110 ("central section" herein is interpreted as any folded area of the filament 108, not necessarily the middle of the filament 108), creating a passing limb 112 and a reducing limb 114. The filament 108 is woven through the substrate 102, from a first surface 116 to a second surface (not shown), at a plurality of passing locations 118. In the depicted embodiment, the filament 108 is woven such that the central section 110 extends from a first terminal passing location 118A on the first end 104 of the substrate 102, creating a first loop 120 (with a first diameter) in the filament 108.

As also shown in FIG. 1, the passing limb 112 and reducing limb 114 are woven through additional passing locations 118 along the substrate 102 toward the second end 106. The passing limb 112 and reducing limb 114 extend from a second terminal passing location 118B at the second end 106 of the substrate 102. Thus, in the planar configuration, as shown in FIG. 1, the first loop 120 of the filament 108 extends from the first end 104 of the substrate 102 and the passing limb 112 and reducing limb 114 extend from the second end 106 of the substrate 102.

Figure 2:
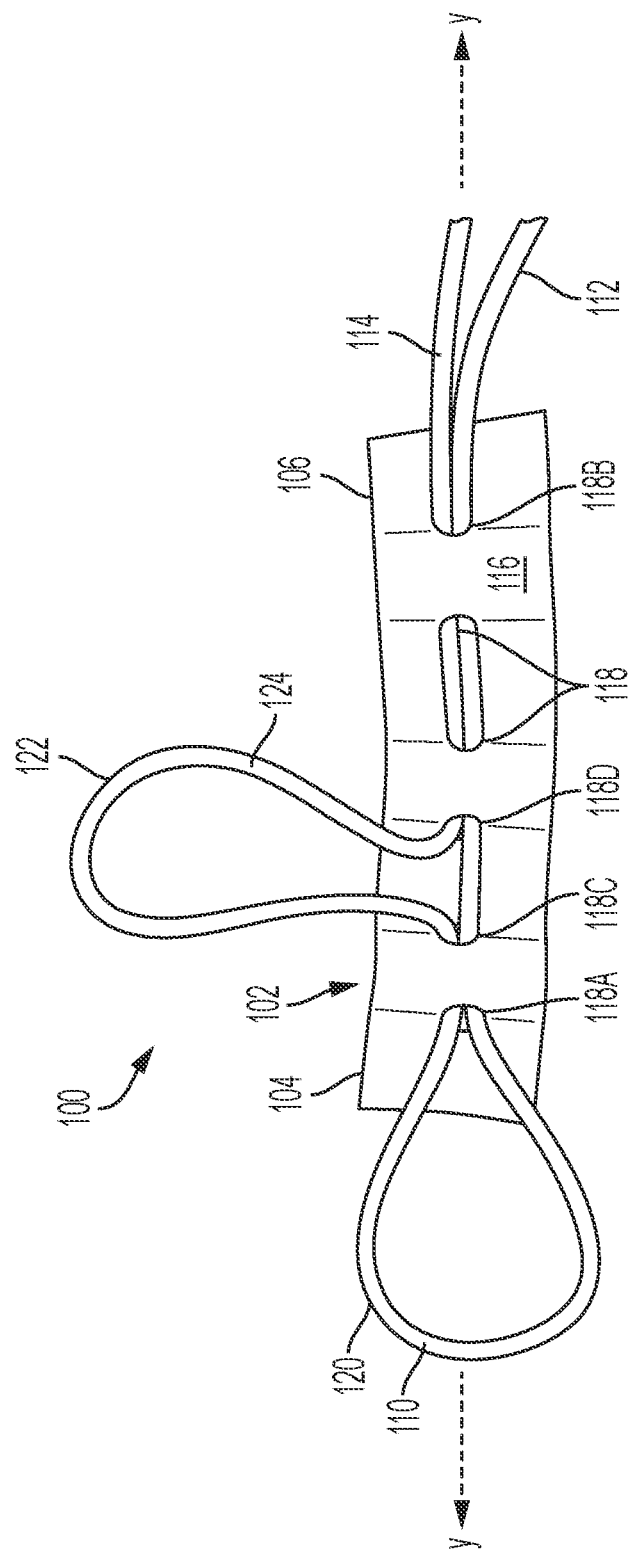
FIG. 2 is a top view schematic representation of the knotless suture anchor construct with a second loop, according to an embodiment.

Turning now to FIG. 2, there is shown a top view schematic representation of the knotless suture anchor construct 100 with a second loop 122, according to an embodiment. With the knotless suture anchor construct 100 in the planar configuration, a passing portion 124 of the reducing limb 114 between two adjacent central passing locations 118C, 118D is pulled from the substrate 102, away from the central longitudinal y-y axis. As the passing portion 124 is pulled away from the substrate 102, a second loop 122 (with a first diameter) is created in the reducing limb 114, as shown.

Figure 3:
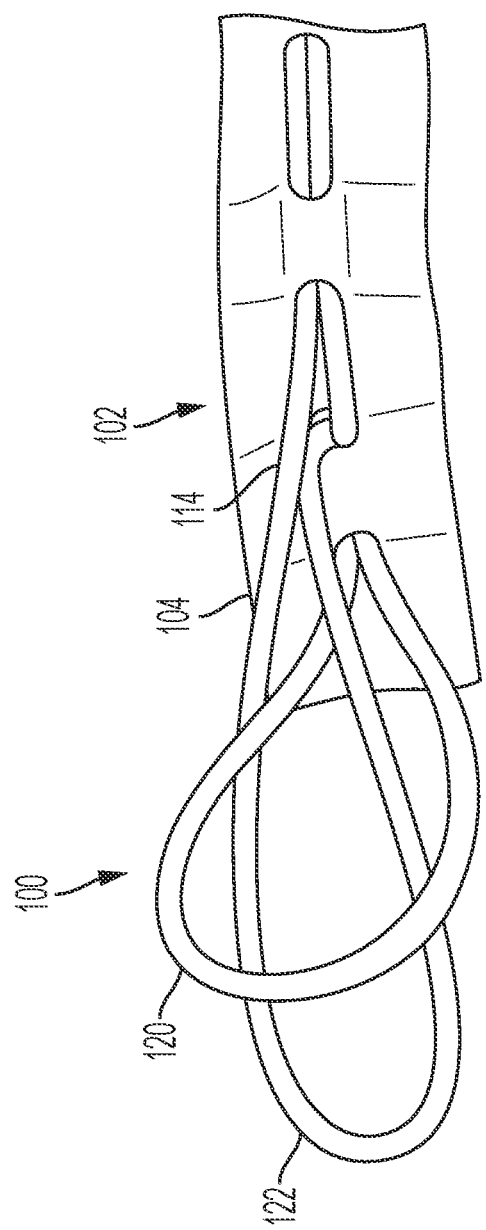
FIG. 3 is a top view schematic representation of the knotless suture anchor construct with the second loop passed through the first loop, according to an embodiment.
Figure 4:
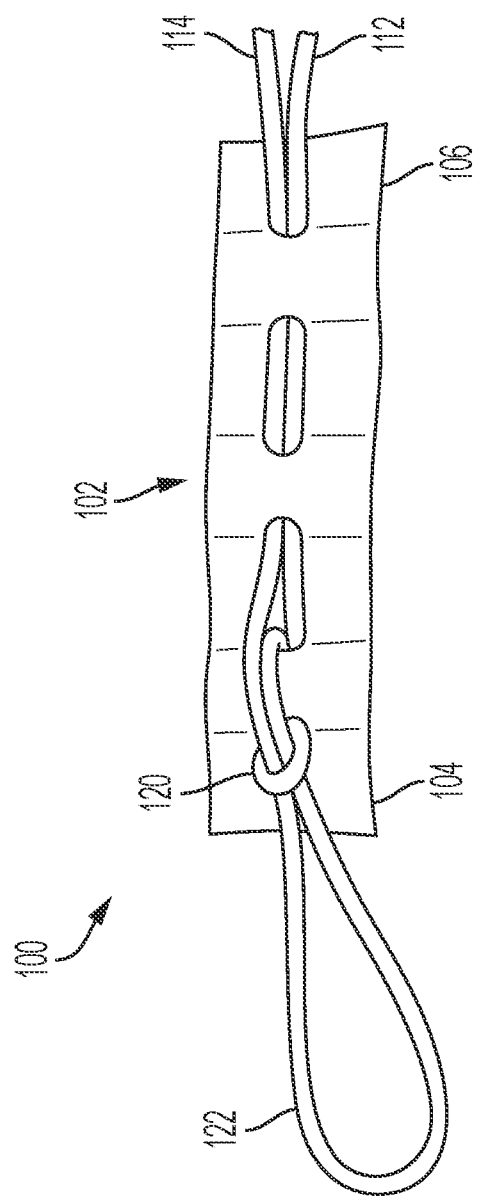
FIG. 4 is a top views schematic representations of the knotless suture anchor construct in a pre-deployment configuration, according to an embodiment.

Referring now to FIGS. 3 and 4, there are shown top views schematic representations of the knotless suture anchor construct 100 with the second loop 122 passed through the first loop 120, according to an embodiment. After the second loop 122 is created in the reducing limb 114 (FIG. 2), the second loop 122 is passed through the first loop 120 at the first end 104 of the substrate 102, as shown in FIG. 3. Thereafter, the first loop 120 is tensioned by pulling the passing limb 112 in a direction away from the second end 106 of the substrate 102. Tensioning the passing limb 112 causes the first loop 120 to decrease in size to a second diameter smaller than the first diameter. As shown in FIG. 4, when the first loop 120 decreases in size, it surrounds or constricts around the second loop 122, moving the knotless suture anchor construct 100 to a pre-deployment configuration.

Figure 5:
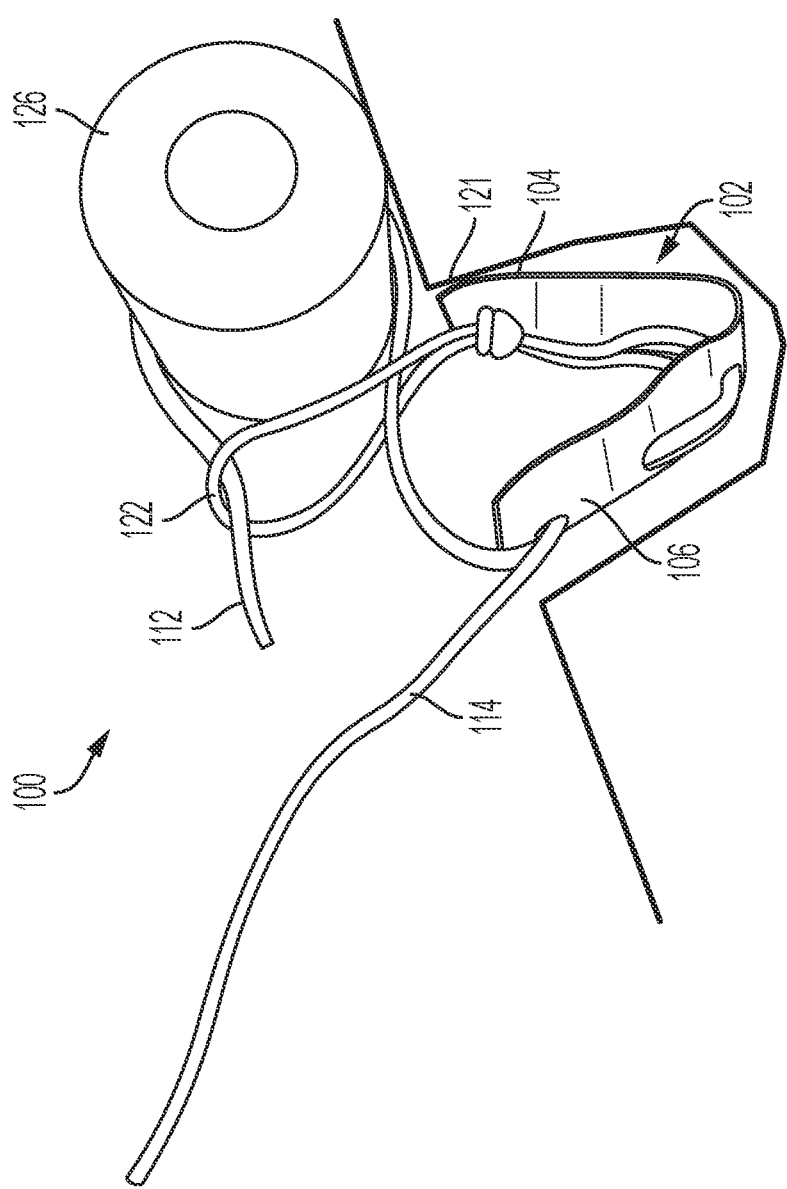
FIG. 5 is a perspective view schematic representation of the knotless suture anchor construct in use around an object, according to an embodiment.
Figure 6:
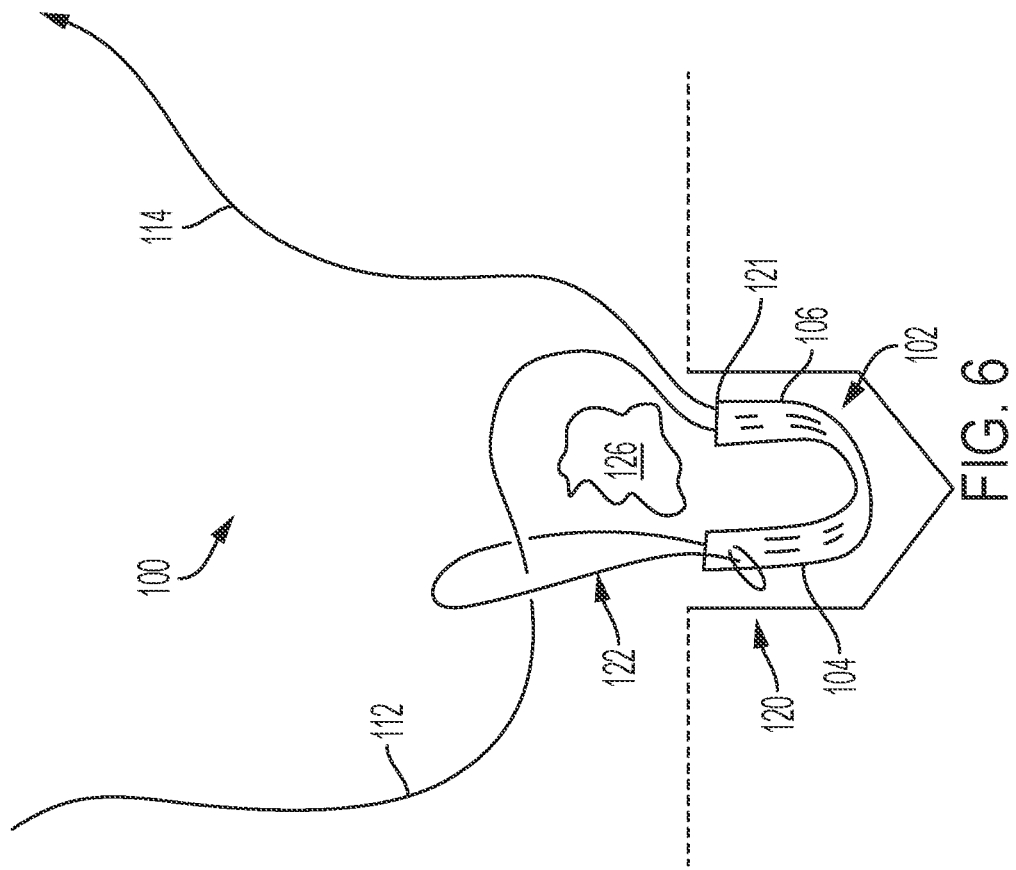
FIG. 6 is a side view schematic representation of the knotless suture anchor construct in use around an object, according to an embodiment.

Turning now to FIGS. 5 and 6, there are shown perspective and side views schematic representations of the knotless suture anchor construct 100 in use around an object 126, according to an embodiment. In the pre-deployment configuration, as shown in FIG. 4, the knotless suture anchor construct 100 is inserted into a bone hole 121 (FIG. 6). As shown in FIGS. 5-6, the knotless suture anchor construct 100 is positioned in a bone hole 121 (FIG. 6) adjacent an object 126, such as a tissue. Although the object 126 may be any other biological material, exemplary embodiments wherein the object 126 is a tissue are discussed below. The knotless suture anchor construct 100 is positioned such that the first end 104 of the substrate 102 is proximal and the second end 106 of the substrate 102 is distal relative to the tissue 126, as shown in FIG. 5. Alternatively, as depicted in FIG. 6, the knotless suture anchor construct 100 can be placed within a bone hole 121 beneath the tissue 126 such that the first end 104 of the substrate 102 extends toward one side of the tissue 126 and the second end 106 of the substrate 102 extends toward an opposing side of the tissue.

With the second loop 122 positioned next to the tissue 126, the knotless suture anchor construct 100 can be deployed. To deploy the knotless suture anchor construct 100, the passing limb 112 is first passed through the second loop 122 and then passed through or around the tissue 126, as shown in FIGS. 5 and 6. Thus, the passing limb 112 and the second loop 122 encircle or otherwise grab the tissue 126. After the passing limb 112 is wrapped around (or passed through) the tissue 126, the passing limb 112 is threaded back through the second loop 122, as shown in FIGS. 5 and 6.

Figure 7:
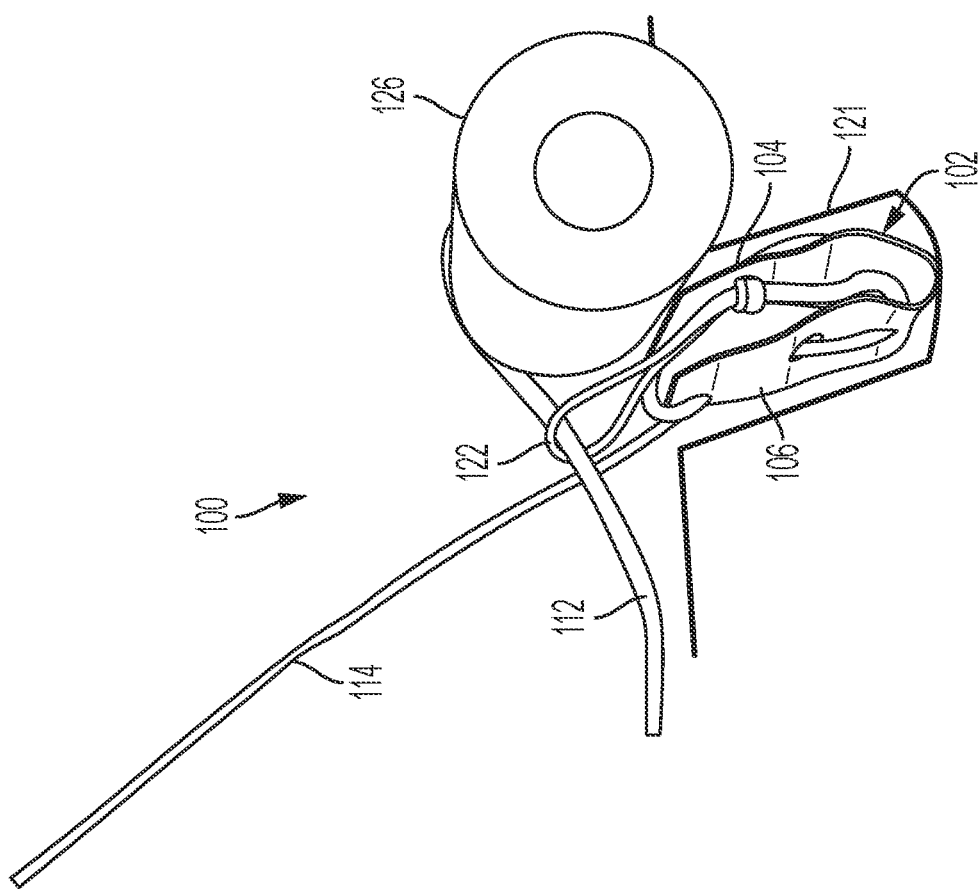
FIG. 7 is another perspective view schematic representation of the knotless suture anchor construct in use around an object, according to an embodiment.
Figure 8:
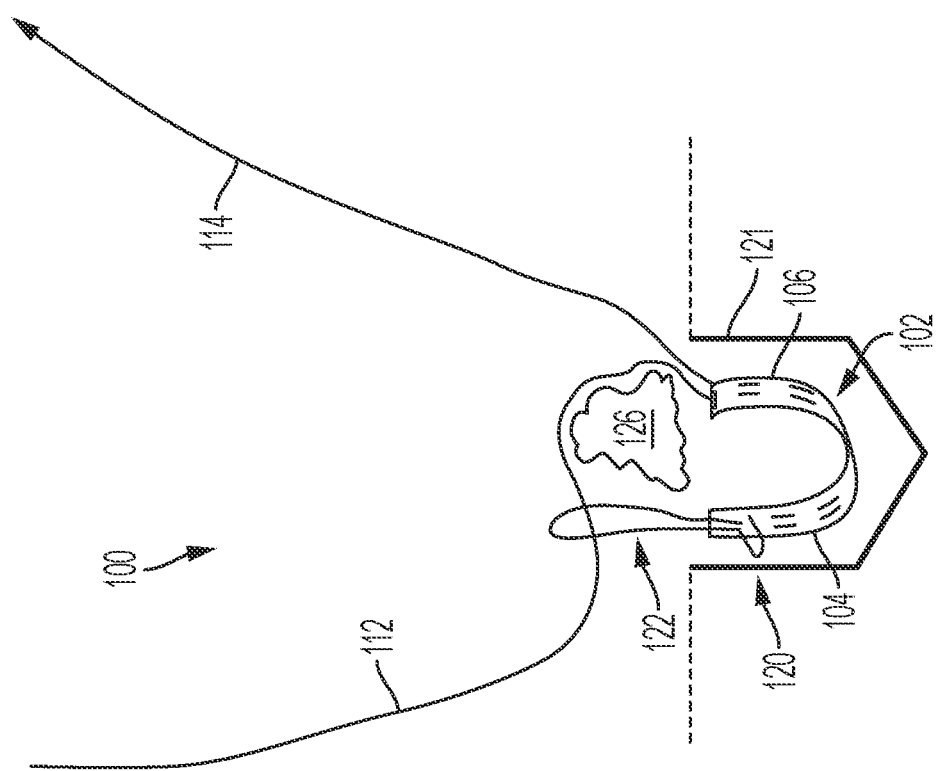
FIG. 8 is another side view schematic representation of the knotless suture anchor construct in use around an object, according to an embodiment.
Figure 9:
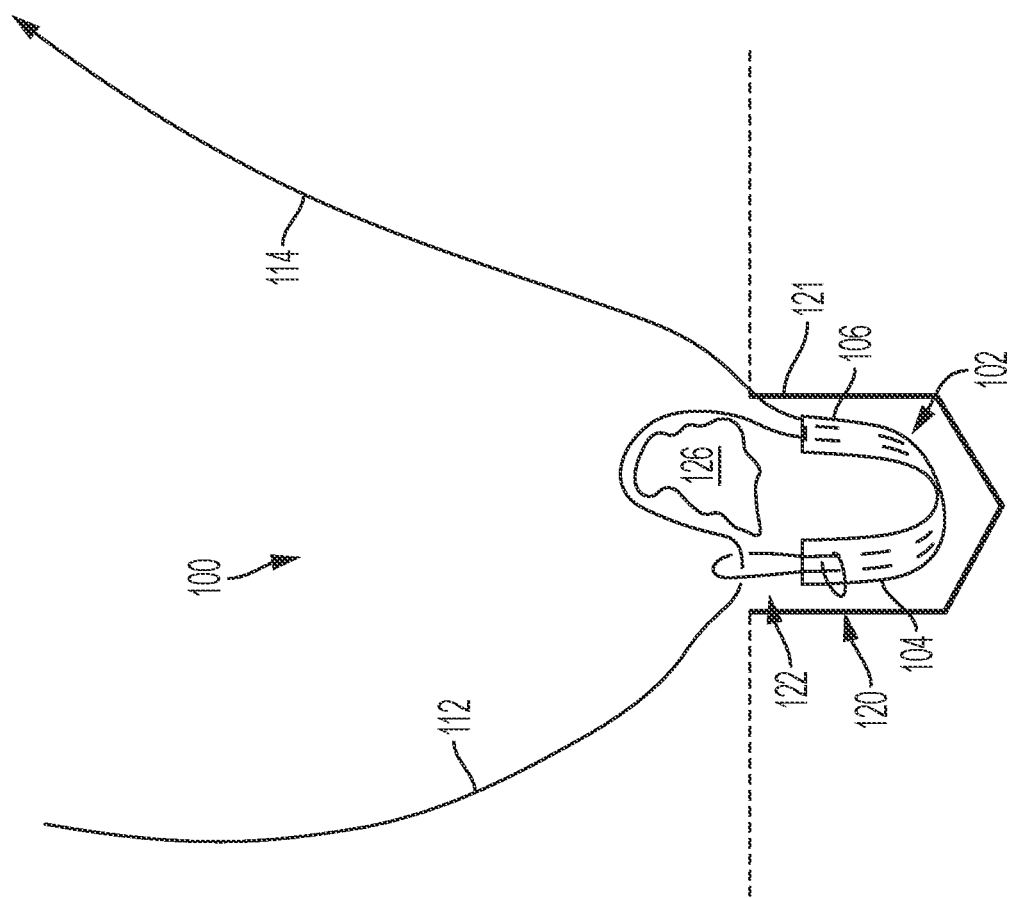
FIG. 9 is yet another side view schematic representation of the knotless suture anchor construct in use around an object, according to an embodiment.

Referring now to FIGS. 7-9, there are shown perspective and side views schematic representations of the knotless suture anchor construct 100 in use around a tissue 126, according to an embodiment. After the passing limb 112 is threaded back through the second loop 122, the reducing limb 114 is tensioned. By pulling the reducing limb 114 in a direction away from the substrate 102, the first diameter of the second loop 122 is reduced to a second diameter. In other words, as the reducing limb 114 is tensioned, the second loop 122 begins to tighten around the passing limb 112, as shown in FIGS. 8-9.

Figure 10:
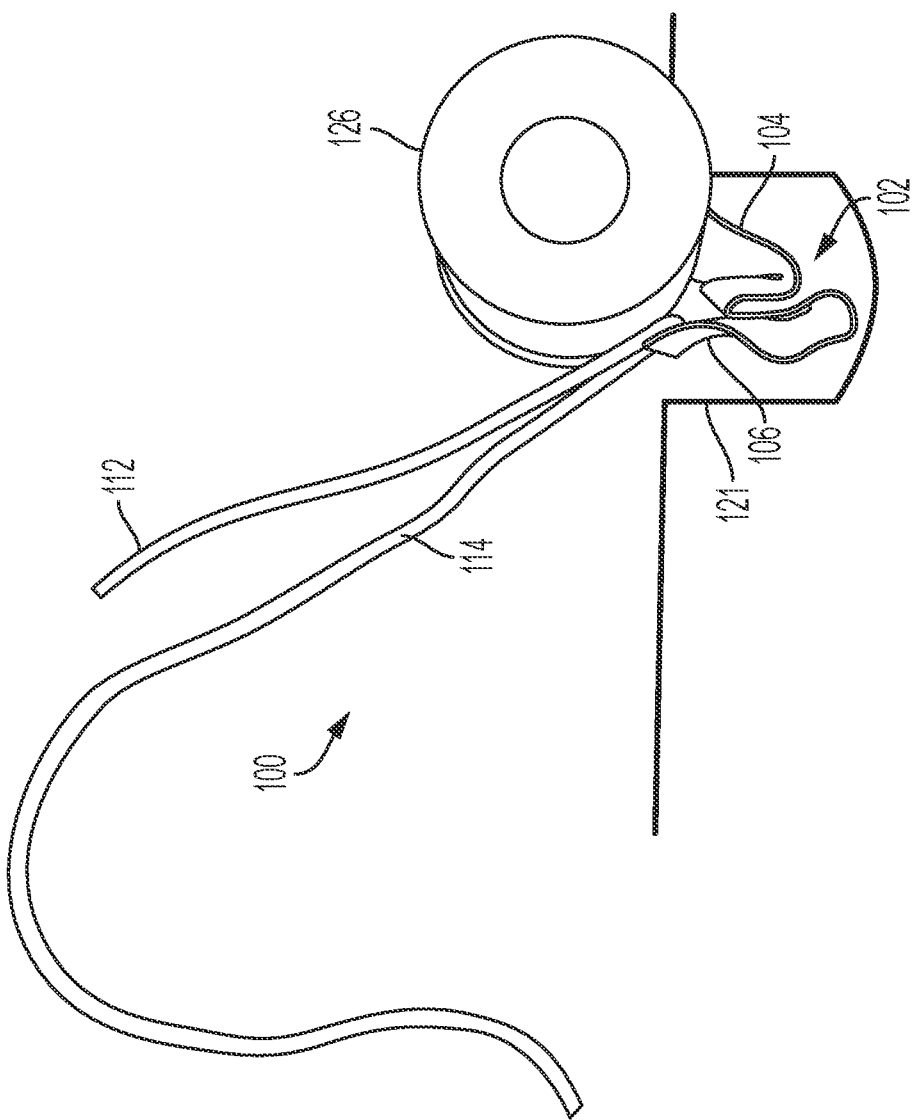
FIG. 10 is a perspective view schematic representation of the knotless suture anchor construct in the deployed configuration around an object, according to an embodiment.
Figure 11:
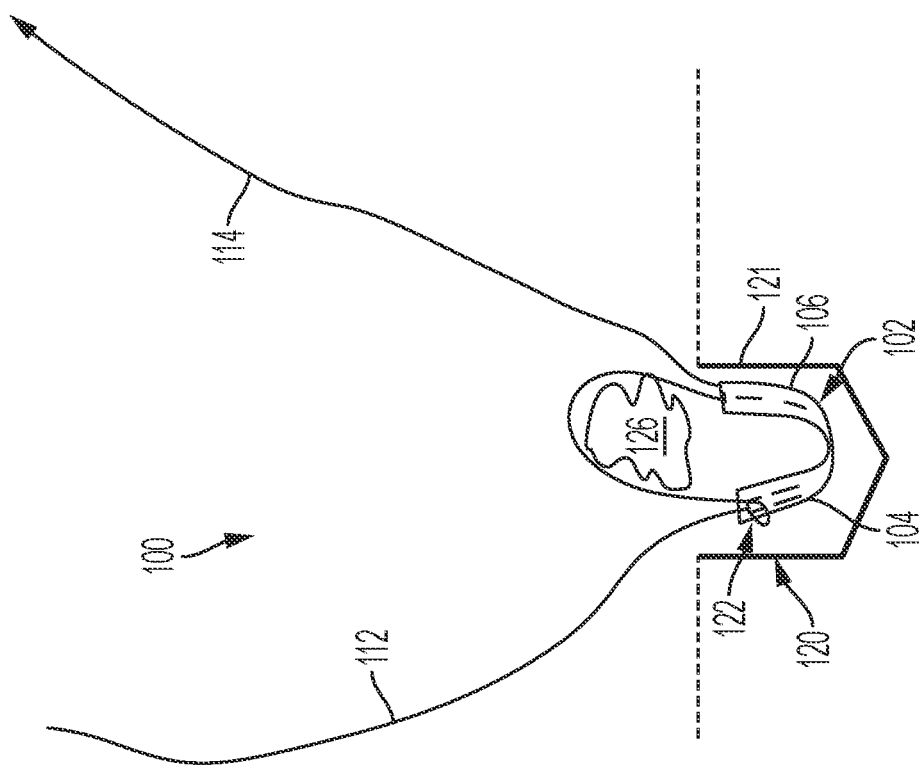
FIG. 11 is a side view schematic representation of the knotless suture anchor construct in the deployed configuration around an object, according to an embodiment.

Referring now to FIGS. 10-11, there is shown perspective and side views schematic representations of the knotless suture anchor construct 100 in a deployed configuration, according to an embodiment. In the deployed configuration, the reducing limb 114 has been tensioned such that the second loop 122 is tightened around the passing limb 112 extending therethrough. As a result of the reduced size of the second loop 122, the tissue 126 is drawn close to or next to the substrate 102 (and the bone hole 121, as shown in FIG. 11), placing the knotless suture anchor construct 100 in a desired position relative to the tissue 126.

Figure 12:
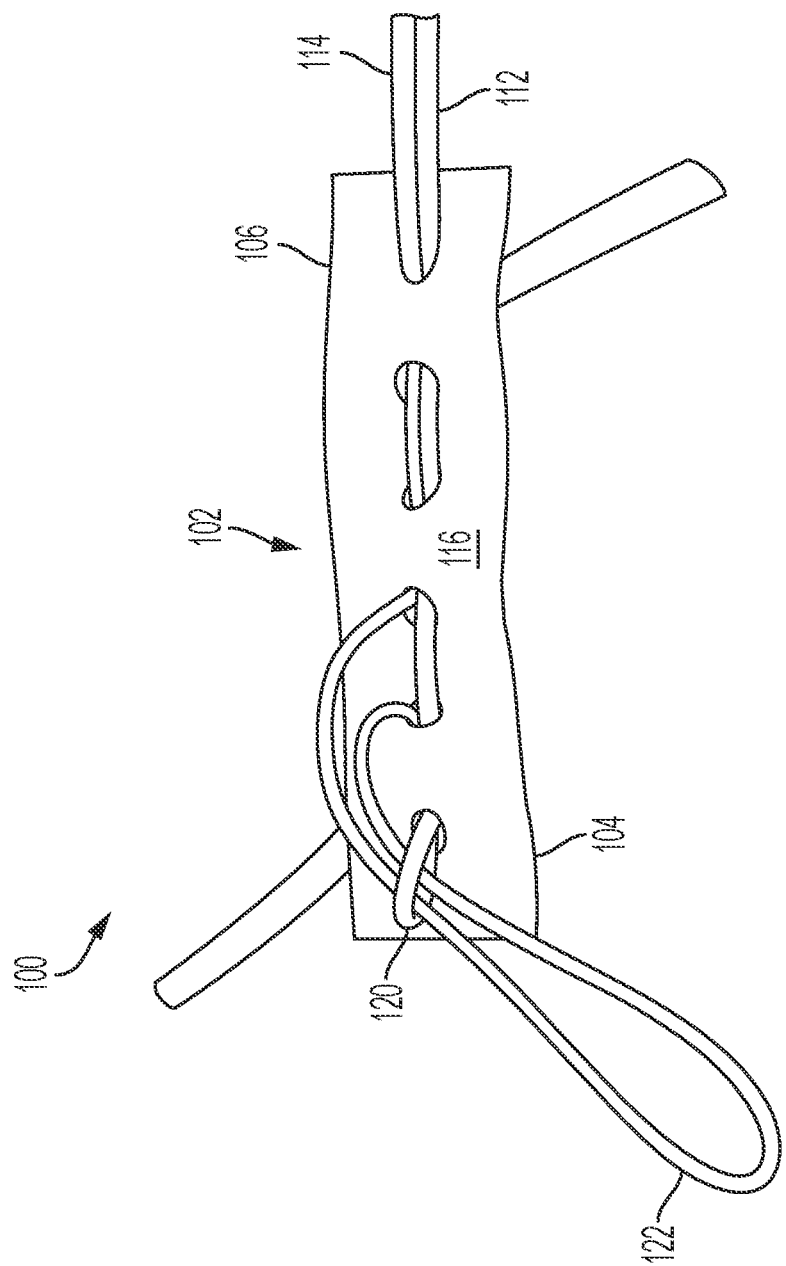
FIG. 12 is a top view schematic representation of the knotless suture anchor construct with a second filament, according to an alternative embodiment.
Figure 13:
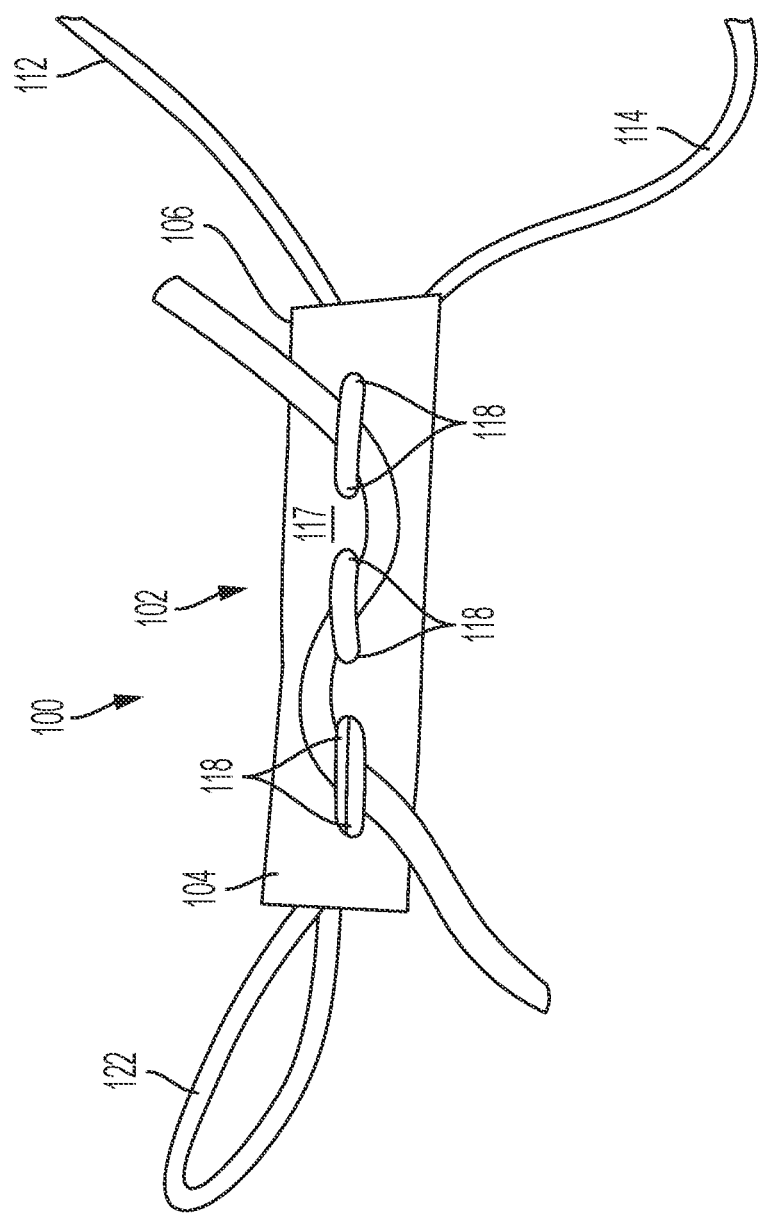
FIG. 13 is a bottom view schematic representation of the knotless suture anchor construct with a second filament, according to an alternative embodiment.

Turning now to FIGS. 12 and 13, there are shown top and bottom views schematic representations of knotless suture anchor construct 100 with a second filament 128 (hereinafter "locking filament"), according to an alternative embodiment. In FIG. 12, the knotless suture anchor construct 100 is in the pre-deployment configuration (as shown in FIG. 4). With the knotless suture anchor construct 100 in the pre-deployment configuration, the locking filament 128 is woven through the passing and reducing limbs 112, 114 extending from the second surface 117 of the substrate 102, as shown in FIG. 13. The locking filament 128 prevents the passing limb 112 and reducing limb 114 from tearing through the substrate 102. The locking filament 128 also prevents the second loop 122 from pulling through the substrate 102. The locking filament 128 can be composed of any type of suture, such as monofilament, braided, or suture tape, for example.

Still referring to FIG. 13, the locking filament 128 passes through the passing and reducing limbs 112, 114 between two adjacent passing locations 118. Stated differently, the locking filament 128 can pass through one or more exposed portions of the passing and reducing limbs 112, 114 on the second surface 117 of the substrate 102. In the embodiment shown in FIG. 13, the locking filament 128 is woven through the passing and reducing limbs 112, 114 between three pairs of adjacent passing locations 118, crossing under the passing and reducing limbs 112, 114 once per pair of adjacent passing locations 118. In another embodiment, the locking filament can pass through exposed portions of the passing and reducing limbs 112, 114 on the first surface of the substrate 102.

Figure 14:
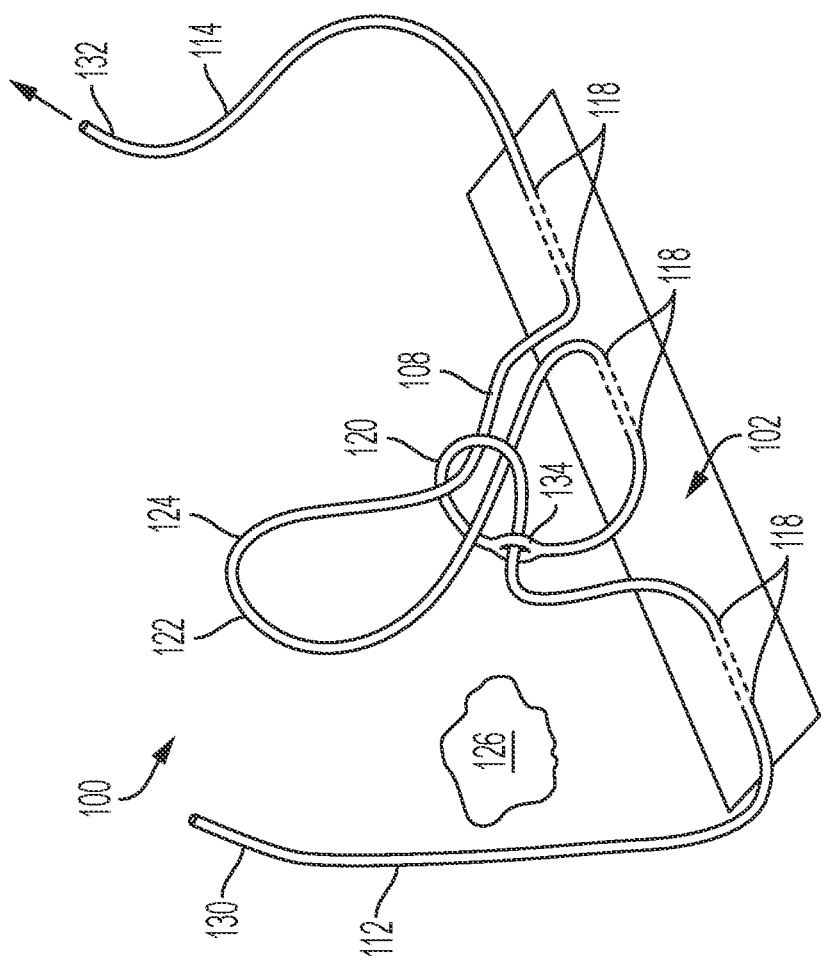
FIG. 14 is a perspective view schematic representation of a knotless suture anchor construct in a pre-deployment configuration, according to an alternative embodiment.
Figure 15:
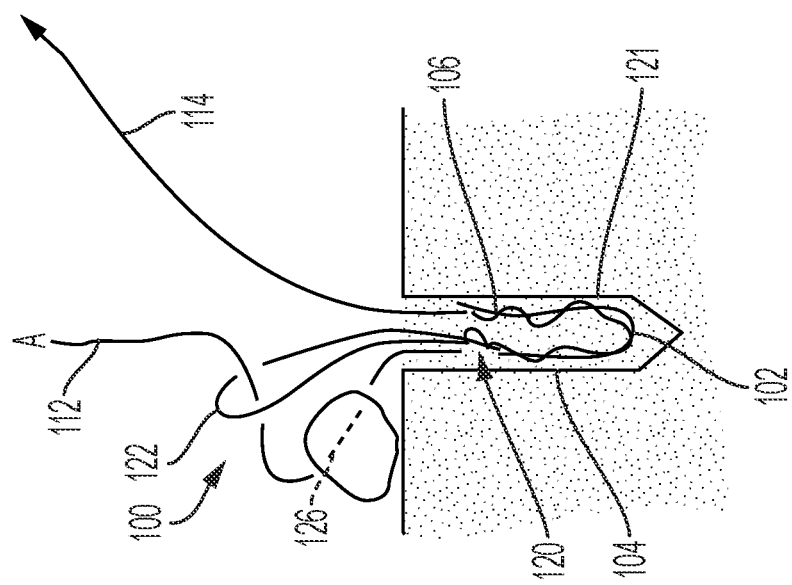
FIG. 15 is a side view schematic representation of a knotless suture anchor construct in a deployed configuration, according to an alternative embodiment.

Referring now to FIGS. 14 and 15, there is shown perspective and side view schematic representations of a knotless suture anchor construct 100 in a pre-deployment configuration and a deployed configuration, respectively, according to an alternative embodiment. The knotless suture anchor construct 100 in FIG. 14 comprises a substrate 102 and a filament 108. The filament 108 comprises a first end 130 and a second end 132 with an eye splice 134 therebetween. The portion of the filament 108 between the first end 130 and the eye splice 134 comprises a passing limb 112 and the portion of the filament 108 between the second end 132 and the eye splice 134 comprises a reducing limb 114.

To achieve the first configuration shown in FIG. 14, the passing limb 112 is first passed through the eye splice 134, creating a first loop 120. The passing limb 112 is then woven through at least one passing location 118 at a first end 104 of the substrate 102. The passing limb 112 is woven such that it extends from the first end 104 of the substrate 102. The reducing limb 114 is woven through the substrate 102 toward a second end 106 of the substrate 102. Specifically, the reducing limb 114 is woven through a passing location 118 adjacent the passing location 118 of the passing limb 112. In the depicted embodiment, the reducing limb 114 is woven through at least two passing locations 118 along the substrate 102 and extends from the second end 106 of the substrate 102, as shown.

Still referring to FIG. 14, a passing portion 124 of the reducing limb 114 between two adjacent passing locations 118 is pulled from the substrate 102. As the passing portion 124 is pulled away from the substrate 102, a second loop 122 is created in the reducing limb 114. To achieve the pre-deployment configuration, the second loop 122 is passed through the first loop 120, as shown. As shown in FIG. 15, for deployment, the knotless suture anchor construct 100 is placed within a bone hole 121 (FIG. 15) in a desired location relative to an object 126, such as a tissue.

In FIG. 14, the knotless suture anchor construct 100 is positioned such that the passing limb 112 and the first end 104 of the substrate 102 are proximal relative to the tissue 126. As shown in FIG. 15, the passing limb 112 is then wrapped around or passed through the tissue 126. Thereafter, the passing limb 112 is passed through the second loop 122. To reduce the size of the second loop 122 (from a first diameter to a second diameter), the reducing limb 114 is pulled in a direction away from the bone hole 121. As the reducing limb 114 is tensioned, the second loop 122 decreases in size and tightens around the passing limb 112, pulling the tissue 126 into apposition with the bone hole 121. When the tissue 126 is in the desired location, the passing and reducing limbs 112, 114 can be trimmed.

Figure 16:
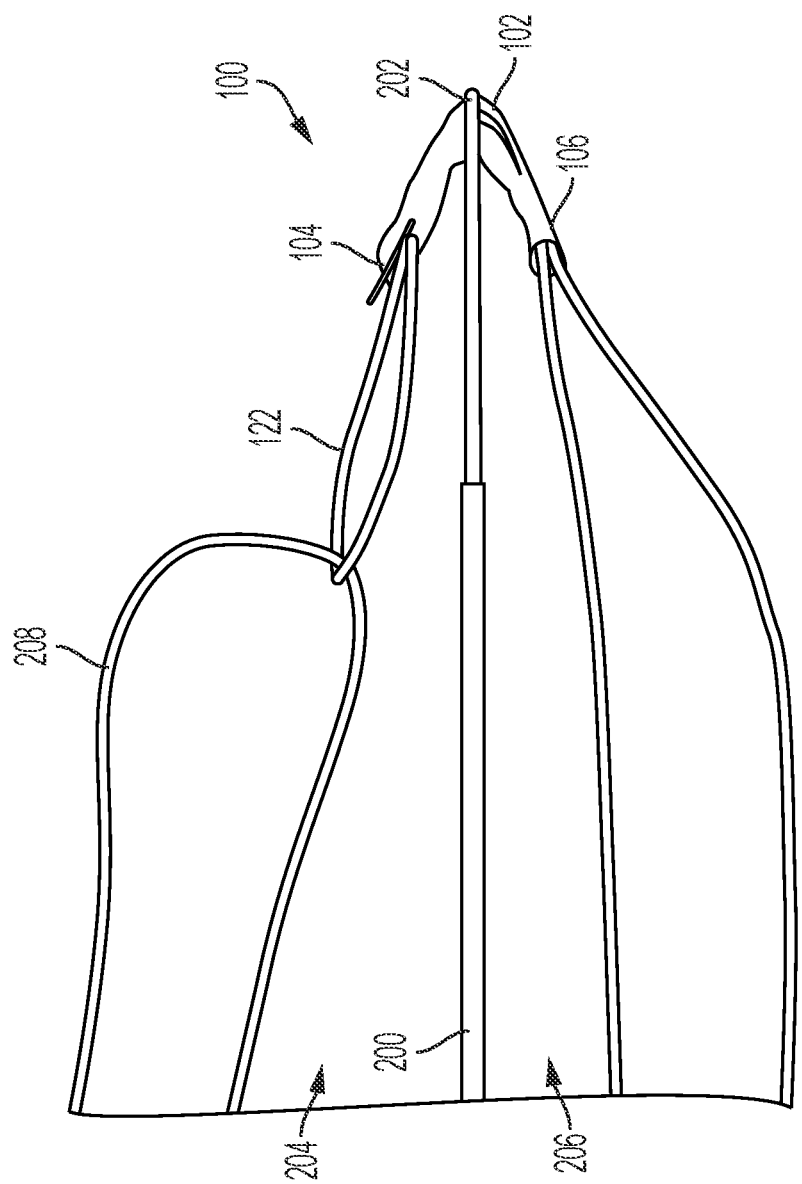
FIG. 16 a side view schematic representation of the knotless suture anchor construct on a driver, according to an embodiment.

Turning now to FIG. 16, there is shown a side view schematic representation of the knotless suture anchor construct 100 on a driver 200, according to an embodiment. In the depicted embodiment, the substrate 102 is placed within the forked end 202 of the driver 200. As shown, the first end 104 of the substrate 102 (and the second loop 122) are on a first side 204 of the driver 200. The second end 106 of the substrate 102 is on a second side 206 of the driver 200. As shown in FIG. 16, the passing limb 112 and reducing limb 114 extend from the second end 106 of the substrate 102 along the second side 206 of the driver 200. In the depicted embodiment, a third filament 208 is passed through the second loop 122. The third filament 208 can be pulled to elongate the second loop 122, while pulling the reducing limb 114 minimizes the second loop 122. Thus, the third filament 208 and the reducing limb 114 can be used to both stabilize the second loop 122 as the knotless suture anchor construct 100 is placed in a bone hole and facilitate deployment of the knotless suture anchor construct 100.

Referring now to FIGS. 17A-20B, there are shown various views schematic representations of the knotless suture anchor construct 100 of alternative embodiments. In the embodiment shown in FIG. 17A, the knotless suture anchor construct 100 comprises a passing portion 124 in the reducing limb 114 that wraps around the first loop 120 in a clockwise fashion, instead of through the first loop 120 in the embodiment of FIGS. 3-4. The knotless suture anchor construct 100 of FIG. 17B also has a passing portion 124 wrapping around the first loop 120, but it wraps around the first loop 120 in the opposite direction (in a counterclockwise fashion) of that shown in FIG. 17A.

Figure 17B:
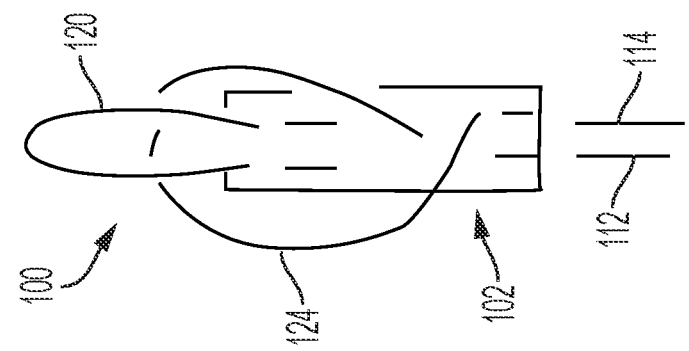
FIG. 17B is a top view schematic representation of the knotless suture anchor construct, according to another alternative embodiment.
Figure 17A:
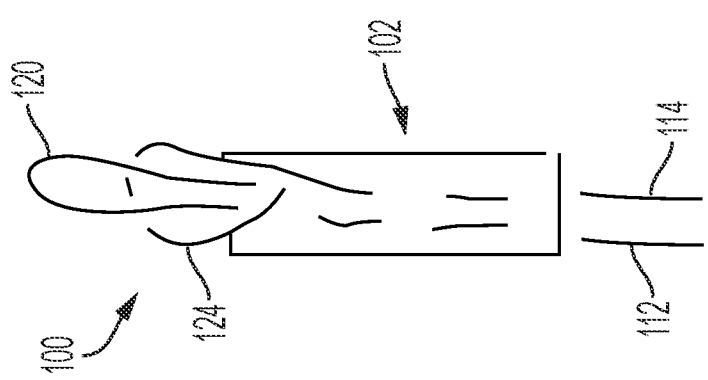
FIG. 17A is a top view schematic representation of the knotless suture anchor construct, according to an alternative embodiment.
Figure 17D:
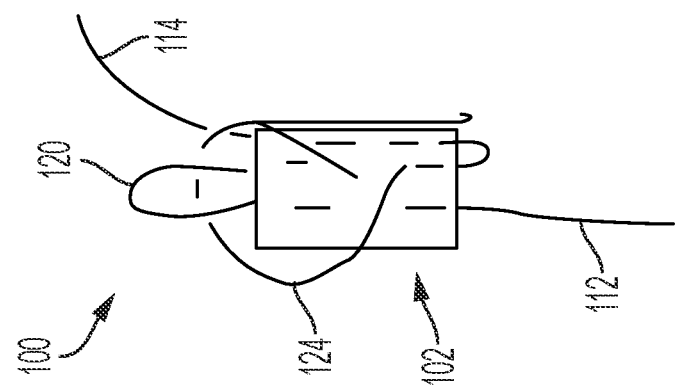
FIG. 17D is a top view schematic representation of the knotless suture anchor construct, according to an additional alternative embodiment.
Figure 17C:
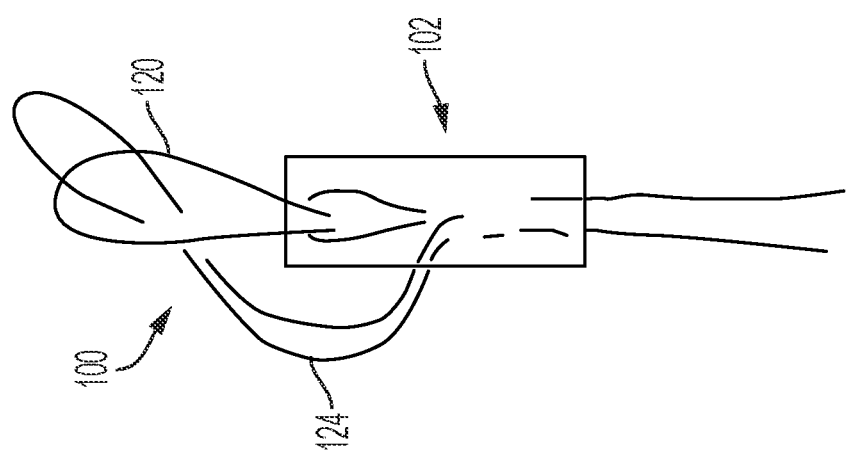
FIG. 17C is a top view schematic representation of the knotless suture anchor construct, according to yet another alternative embodiment.

In the embodiment shown in FIG. 17C, the passing portion 124 extends through the first loop 120; however, the passing portion 124 is passed through the first loop 120 from below (i.e., from a direction opposite that shown in FIG. 3). In FIG. 17D, an embodiment of the knotless suture anchor construct 100 is shown wherein the filament 108 is woven through the substrate 102 in a first direction, a second direction, and back in the first direction again. The filament 108 is passed through the substrate 102 such that a first loop 120 is created and the passing limb 112 and reducing limb 114 extend from opposing sides of the substrate 102.

Figure 18:
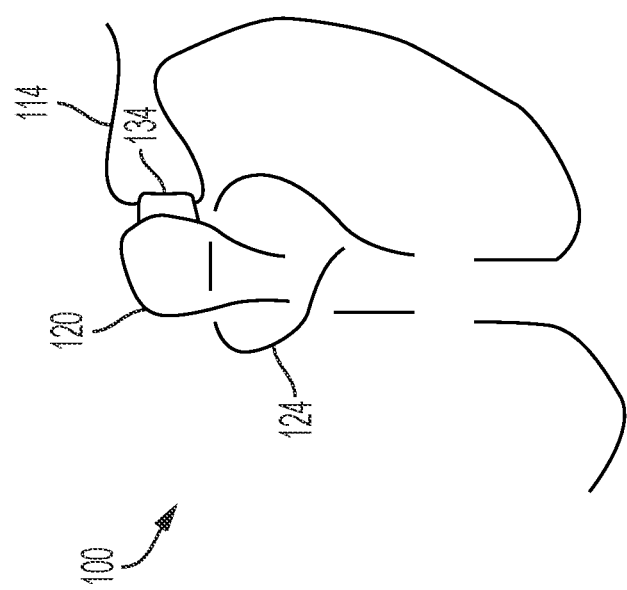
FIG. 18 is a top view schematic representation of the knotless suture anchor construct with a finger trap, according to an alternative embodiment.
Figure 19:
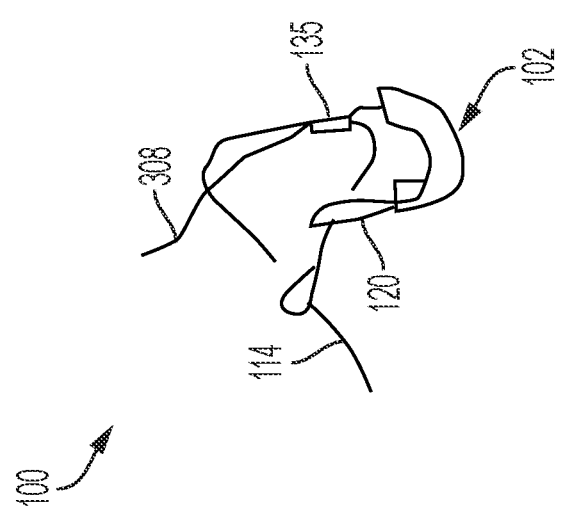
FIG. 19 is a top view schematic representation of the knotless suture anchor construct with a finger trap, according to another alternative embodiment.

In FIG. 18, the knotless suture anchor construct 100 comprises an eye splice 134 in the first loop 120. The passing portion 124 of the reducing limb 114 is wrapped around the first loop 120. Thereafter, the reducing limb 114 is passed through the eye splice 134, as shown. In FIG. 19, the passing limb (not shown) and the reducing limb 114 extend from opposing sides of the substrate 102. Further, the knotless suture anchor construct 100 comprises a "finger trap" 135 on the reducing limb 114. A third filament 308 is threaded through the finger trap 135 and the first loop 120 and grabs the reducing limb 114. The third filament 308 is used to pull the reducing limb 114 and the first loop 120 through the finger trap 135.

Figure 20B:
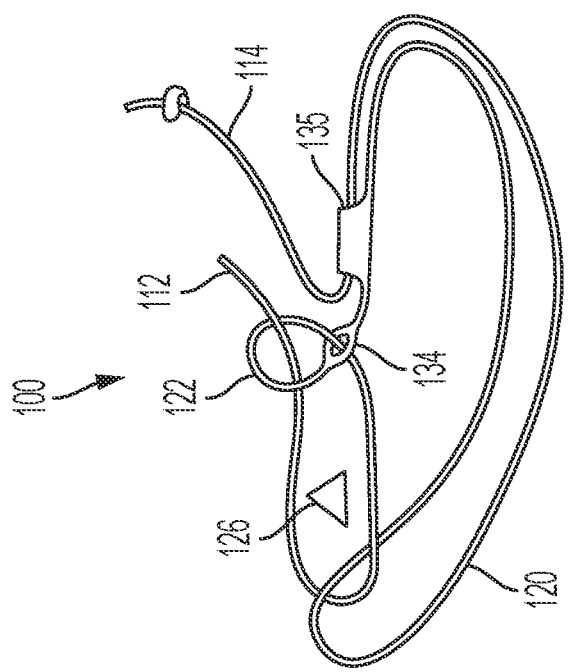
FIG. 20B is a perspective view schematic representation of the knotless suture anchor of FIG. 20A in the deployed configuration, according to an alternative embodiment.
Figure 20A:
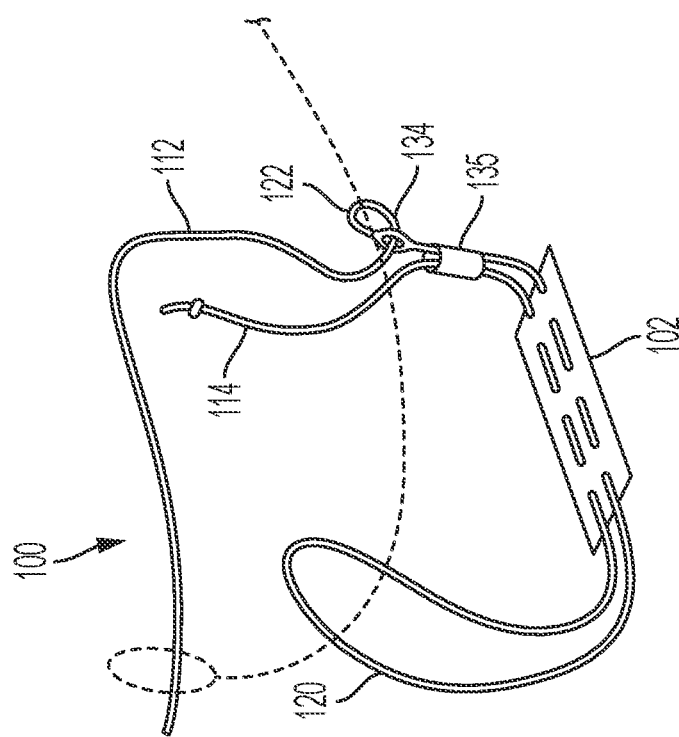
FIG. 20A is a perspective view schematic representation of the knotless suture anchor construct with a finger trap and an eye splice in the pre-deployment configuration, according to an alternative embodiment.

In FIGS. 20A-20B, the knotless suture anchor construct 100 comprises a finger trap 135 wherein the passing limb 112 and the reducing limb 114 are threaded therethrough. The passing limb 112 and reducing limb 114 extend from the finger trap 135 in the pre-deployment configuration, as shown in FIG. 20A. The knotless suture anchor construct 100 also comprises an eye splice 134 in the passing limb 112. The passing limb 112 is threaded through the eye splice 134 to form a second loop 122. To deploy the knotless suture anchor construct 100, the passing limb 112 is threaded through the first loop 120, around the object 126, and through the second loop 122, as shown in FIG. 20B. Tensioning the reducing limb 114, decreases the size of the first loop 120 and move the object 126 into toward the finger trap 135.

Other configurations of the knotless suture anchor construct 100 are contemplated and may include a variation of elements, such as the finger trap or eye splice.

All definitions, as defined and used herein, should be understood to control over dictionary definitions, definitions in documents incorporated by reference, and/or ordinary meanings of the defined terms.

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as, "has" and "having"), "include" (and any form of include, such as "includes" and "including"), and "contain" (any form of contain, such as "contains" and "containing") are open-ended linking verbs. As a result, a method or device that "comprises", "has", "includes" or "contains" one or more steps or elements. Likewise, a step of method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts and equivalents of all means or step plus function elements in the claims below, if any, are intended to include any structure, material or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the present invention for various embodiments with various modifications as are suited to the particular use contemplated.

What is claimed is:

1. A knotless suture anchor construct, comprising:
   a substrate having a first end and a second end;
   a filament woven through a plurality of passing locations along the substrate, the filament forming a first loop extending to a passing limb and to a reducing limb;
   a passing portion in the reducing limb between two adjacent passing locations of the plurality of passing locations;
   wherein in a pre-deployment configuration, the first loop of the filament extends from a first surface and the first end of the substrate and the passing limb and the reducing limb extend from the first surface or a second surface and the second end of the substrate; and
   wherein in the pre-deployment configuration, the passing portion extends through the first loop, forming a second loop in the reducing limb.

2. The construct of claim 1, wherein in the pre-deployment configuration, the passing limb is tensioned such that the first loop is configured to reduce in size from a first diameter to a second diameter.

3. The construct of claim 2, wherein in the pre-deployment configuration, the first loop is wrapped around the second loop.

4. The construct of claim 1, wherein the filament is composed of hollow suture braid.

5. The construct of claim 1, wherein the first loop extends from a first passing location of the plurality of passing locations at the first end of the substrate.

6. The construct of claim 5, wherein the reducing limb and passing limb extend from a second passing location of the plurality of passing locations at the second end of the substrate.

7. The construct of claim 6, wherein in a deployed configuration, the passing limb is configured to extend around an object and through the second loop.

8. The construct of claim 7, wherein in the deployed configuration, the reducing limb is tensioned such the second loop is configured to reduce in size from a first diameter to a second diameter.

9. The construct of claim 1, further comprising an elongated locking filament woven through exposed portions of the passing limb and reducing limb extending from the second surface of the substrate.

10. A method for securing an object in position relative to a bone hole, comprising the steps of:
    providing a knotless suture anchor construct comprising a substrate having a first end and a second end, a filament woven through a plurality of passing locations along the substrate, the filament forming a first loop extending to a passing limb and reducing limb, wherein the first loop of the filament extends from the first end of the substrate and the passing limb and the reducing limb extend from the second end of the substrate, a passing portion in the reducing limb between two adjacent passing locations of the plurality of passing locations, and wherein the passing portion extends through the first loop forming a second loop in the reducing limb;
    inserting the knotless suture anchor construct into a bone hole;
    passing the passing limb around the object and then through the second loop; and
    tensioning the reducing limb to decrease the size of the second loop.

11. The method of claim 10, further comprising the step of loading the knotless suture anchor construct onto a driver.

12. The method of claim 10, wherein the substrate is loaded into a forked end of the driver.

13. The method of claim 10, further comprising the step of trimming the reducing limb and the passing limb.

* * * * *